United States Patent
Wilke et al.

(10) Patent No.: US 10,531,899 B2
(45) Date of Patent: Jan. 14, 2020

(54) SLOTTED AUGMENTATION SLEEVE

(71) Applicant: Stryker European Holdings I, LLC, Kalamazoo, MI (US)

(72) Inventors: André Wilke, Kiel (DE); Astrid Bordush, Buckinghamshire (GB)

(73) Assignee: Stryker European Holdings I, LLC, Kalamazoo, MI (US)

( * ) Notice: Subject to any disclaimer, the term of this patent is extended or adjusted under 35 U.S.C. 154(b) by 417 days.

(21) Appl. No.: 15/502,664

(22) PCT Filed: Aug. 8, 2014

(86) PCT No.: PCT/EP2014/067083
§ 371 (c)(1),
(2) Date: Feb. 8, 2017

(87) PCT Pub. No.: WO2016/020014
PCT Pub. Date: Feb. 11, 2016

(65) Prior Publication Data
US 2017/0231671 A1    Aug. 17, 2017

(51) Int. Cl.
*A61B 17/86* (2006.01)
*A61B 17/88* (2006.01)
*A61B 17/70* (2006.01)

(52) U.S. Cl.
CPC ...... *A61B 17/7097* (2013.01); *A61B 17/7091* (2013.01); *A61B 17/864* (2013.01);
(Continued)

(58) Field of Classification Search
CPC .......................... A61B 17/864; A61B 17/8645
See application file for complete search history.

(56) References Cited

U.S. PATENT DOCUMENTS

| 4,653,489 A | 3/1987 | Tronzo |
| 6,048,343 A * | 4/2000 | Mathis ............... A61B 17/7098 606/304 |

(Continued)

FOREIGN PATENT DOCUMENTS

WO    2004002340 A1    1/2004

OTHER PUBLICATIONS

Bailey et al., "Biomechanical evaluation of a new composite bioresorbable screw", The Journal of Hand Surgery, vol. 31B, No. 2, Apr. 2006, pp. 208-212.

(Continued)

*Primary Examiner* — Nicholas W Woodall
(74) *Attorney, Agent, or Firm* — Lerner, David, Littenberg, Krumholz & Mentlik, LLP (57) ABSTRACT

A combination of an implant (100) like a bone screw together with an augmentation sleeve (200) is suggested. The bone screw may comprise a trailing end portion with a plurality of lateral bores (120). The augmentation sleeve may comprise a leading end portion which is adapted to be coupled to the trailing end portion of the bone screw, and a lateral opening (220) at the leading end. The augmentation sleeve may be adapted to guide an augmentation tool to the trailing end portion of the bone screw and to the leading end portion of the augmentation sleeve so that the trailing end portion of the bone screw may be augmented by pressing augmentation material through the plurality of lateral bores at the trailing end portion of the bone screw and further through the lateral opening of the augmentation sleeve into the bone at the trailing end of the bone screw, or other implant. After the augmentation of the trailing end portion of the bone screw, the augmentation sleeve may be removed.

17 Claims, 4 Drawing Sheets

(52) U.S. Cl.
CPC ...... *A61B 17/8645* (2013.01); *A61B 17/8802* (2013.01); *A61B 17/8811* (2013.01); *A61B 17/8888* (2013.01)

(56) References Cited

U.S. PATENT DOCUMENTS

| | | | |
|---|---|---|---|
| 6,048,346 A * | 4/2000 | Reiley | A61B 17/8811 606/83 |
| 6,214,012 B1 * | 4/2001 | Karpman | A61B 17/864 606/246 |
| 6,679,890 B2 | 1/2004 | Margulies et al. | |
| 7,250,055 B1 | 7/2007 | Vanderwalle | |
| 7,338,495 B2 * | 3/2008 | Adams | A61B 17/32002 606/180 |
| 7,717,947 B1 | 5/2010 | Wilberg et al. | |
| 8,057,480 B2 | 11/2011 | Dorawa et al. | |
| 8,382,808 B2 | 2/2013 | Wilberg et al. | |
| 8,551,124 B2 | 10/2013 | Wieland | |
| 8,556,909 B2 | 10/2013 | Giersch et al. | |
| 8,556,947 B2 | 10/2013 | Dorawa et al. | |
| 8,690,930 B2 * | 4/2014 | Biedermann | A61B 17/7037 606/304 |
| 8,747,411 B2 * | 6/2014 | Mitchell | A61B 17/7098 606/104 |
| 9,271,835 B2 * | 3/2016 | Bagga | A61B 17/68 |
| 2006/0122614 A1 | 6/2006 | Truckai et al. | |
| 2009/0018590 A1 | 1/2009 | Dorawa et al. | |
| 2009/0275994 A1 | 11/2009 | Phan et al. | |
| 2010/0256688 A1 * | 10/2010 | Giersch | A61B 17/68 606/305 |
| 2012/0316513 A1 | 12/2012 | Sharkey et al. | |
| 2013/0006278 A1 * | 1/2013 | Mayer | A61B 17/686 606/151 |
| 2013/0345710 A1 | 12/2013 | Kleiner et al. | |
| 2014/0114362 A1 | 4/2014 | Giersch et al. | |

OTHER PUBLICATIONS

Bonfield et al., "Biomaterials—a new generation", Materials World Jan. 1997; 5 No. 1, pp. 18-20 (6 pages total).

Fang et al., "Processing and mechanical properties of HA/UHMWPE nanocomposites", Biomaterials 27, pp. 3701-3707, Jul. 2006.

Huang et al., "Novel Porous Hydroxyapatite Prepared by Combining $H_2O_2$ Foaming with PU Sponge and Modified with PLGA and Bioactive Glass", Journal of Biomaterials Applications vol. 21, Apr. 2007, pp. 351-374.

Huang et al., "Synthesis and characterization of nano-HA/PA66 composites", Journal of Materials Science: Materials in Medicine 14, pp. 655-660, Jul. 2003.

International Preliminary Report on Patentability for Application No. PCT/EP2014/067083 dated Oct. 21, 2016, 12 pages.

International Search Report for Application No. PCT/EP2014/067083 dated Oct. 1, 2014.

Juhasz et al., "Mechanical properties of glass-ceramic A-W-polyethylene composites: effect of filler content and particle size", Biomaterials, Mar. 2004; 25(6), pp. 949-955.

Rea et al., "Bioactivity of ceramic-polymer composites with varied composition and surface topography", Journal of Materials Science: Materials in Medicine 15, Sep. 2004; pp. 997-1005.

Wintermantel et al., "Medizinaltechnik mit biokompatiblen Materialien und Verfahren", 3. Auflage, Springer, Berlin Jan. 2002, p. 200; for information on PGA and PLA see pp. 202 ff., on PCL see p. 207, on PHB/PHV copolymers p. 206; on polydioxanone PDS p. 209.

* cited by examiner

SLOTTED AUGMENTATION SLEEVE

CROSS-REFERENCE TO RELATED APPLICATIONS

The present application is a national phase entry under 35 U.S.C. § 371 of International Application No. PCT/EP2014/067083 filed Aug. 8, 2014, published in English as WO 2016/020014 A1, the disclosure of which is hereby incorporated herein by reference.

FIELD OF THE DISCLOSURE

The invention relates, in particular, to a sleeve for an augmentation of an implant, for example a bone screw. Furthermore, the invention relates to a corresponding method for operating the sleeve to augment a portion of an implant.

BACKGROUND INFORMATION

Known from U.S. Pat. No. 4,653,489 is a system wherein fixation cement is introduced through a screw into a portion of a bone afflicted by osteoporoses. Femoral neck fractures as well as distal femoral fractures can be fixated by means of this device.

The system in accordance with prior art comprises a screw having a flow cavity, i.e. an axial through-bore through which bone cement can be introduced into the portion at the tip of the screw. The bone cement is advanced by a device which is releasably attached to the subsequent end of the screw. This device is similar to commercially available syringes. In use of this prior art device, the fixation cement is injected in an already fluidized state into the axial through-bore of the screw. Due to the pressure, the fixation cement is adequately fluidized, so that it can pass through the trailing end of the screw into the bone, as a result of which the screw is augmented in the bone.

This system has a drawback that the distribution of the fixation cement within the portion of the bone is neither reliable nor sufficiently controllable. It is in particular a drawback that the implant together with the fixation cement may shift within osteoporotic bone tissue as soon as forces apply onto the bone and thus onto the implant.

SUMMARY OF THE INVENTION

An object of the invention may be to provide a device and a method by means of which an implant can be augmented such that a fixation of the implant within the bone is improved. Another object may be to provide a device and a method by means of which a reliable augmentation of an implant in an installation site can be assured. This is achieved by the subject-matter of the respective independent claims. Further embodiments are described in the dependent claims.

In general, an implant like a bone screw together with an augmentation sleeve is provided. The bone screw may comprise a leading end portion with an outer thread and a trailing end portion, wherein at least the trailing end portion comprises an axial bore and a plurality of lateral bores formed on a circumference of the bone screw. The augmentation sleeve may comprise a leading end portion which is adapted to be coupled to the trailing end portion of the bone screw, and a lateral opening at the leading end.

The augmentation sleeve may be adapted to guide an augmentation tool to the trailing end portion of the bone screw and to the leading end portion of the augmentation sleeve so that augmentation material may be inserted, by means of the augmentation tool, through a plurality of lateral bores at the trailing end portion of the bone screw. Furthermore, augmentation material may be inserted through a lateral opening of the augmentation sleeve into the bone at the trailing end of the bone screw, or other implant. By way of this, a support of the screw beneath hard bone tissue, for example a cortical bone, may be provided so that bone which engages the thread at the leading end of the screw may be stabilized with a predetermined distance from other bone structures.

After the augmentation of the trailing end portion of the bone screw, the augmentation sleeve may be removed.

As used herein, the term "augmentation" can, for example, encompass any kind of anchoring. The term "augmentation" can, for example, encompass an anchoring by way of material which is arranged between an implant and an object, like a dowel between a screw and a wall. Furthermore, the term "augmentation" can, for example, encompass an anchoring by providing material which engages the implant as well as the surrounding tissue, but which material is introduced after the implant is inserted into the object.

Consequently, an "augmentation implant" can be any kind of an implant, like bone screws or bone nails, which may be anchored by providing material between the implant and tissue surrounding the implant, i.e. which may be augmented. Accordingly, the overall volume of the augmentation implant is increased after the implant is inserted into tissue of an object, for example bone, wood or another porous material.

As used herein, the verb "to augment" can, for example, encompass any kind of anchoring or fixating of an implant in an object by providing material and thus increasing the overall volume of the implant, for example with a material which can be pressed from the implant into at least one cavity or into pores in tissue of an object, with the material being fluidized, wherein the material is capable of subsequently hardening.

A material for augmenting an implant may be provided in form of an augmentation pin. An augmentation pin may be, for example, a small pin of approximately 3 cm to 4 cm, length with a few millimetres in diameter. It will be understood, that the dimensions of the augmentation pin depend upon the intended application, i.e. depends on the amount of material which is needed for a reliable augmentation of a particular implant.

It is noted, that the material of the augmentation pin may be a polymer material being fluidizable and biocompatible, wherein a biocompatible material may be a material which does not negatively interfere with human or animal tissue. Additionally, the material may also be bioabsorbable.

In this text the expression "polymer material being fluidizable e.g. by mechanical vibration" or in short "fluidizable polymer material" or "fluidizable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration may be between 2 kHz and 200 kHz, preferably 20 to 40 kHz and the amplitude between 1 μm and 100 μm, preferably around 10 to 30 μm. Such vibrations may be e.g. produced by ultrasonic devices as e.g. known for dental applications. For being able to constitute a loadbearing connection to the tissue, the material at the time of insertion may have an elasticity coefficient of more than 0.5 GPa, preferably more than 1 GPa. The elasticity coefficient of at least 0.5 GPa also ensures that the fluidizable or liquefiable material may be capable of transmitting the ultrasonic oscillation with such little damping that inner fluidization or liquefaction and thus destabilization of the liquefiable element does not occur, i.e. liquefaction occurs only where the liquefiable/fluidizable material is at the liquefaction interface to the stop face. The plastification temperature is preferably of up to 200° C., between 200° C. and 300° C. or even more than 300° C.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suitable thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, 8208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM Polyacetal, tradenames Delrin, Tenac, has also been used in endoprostheses by Protec).

The fluidizable/liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

The material of the liquefiable element(s), i.e. of an augmentation pin, may contain an additional substance, for example for promoting healing or regeneration of for furthering x-ray visibility. For example, the additional substance may be a growth factor, an antibiotic, an inflammation inhibitor or a buffer. More particularly, the additional substance be a drug promoting healing, in particular growth, differentiation and/or regeneration such as a proteinaceous drug like a growth and/or differentiation factor, e.g. of the Bone Morphogenic Protein family (especially BMP 2, 6, 7, for certain applications also BMP 12, 13), an Insulin Growth Factor (e.g. IGF 1), a Platelet Derived Growth Factor (PDGF), a Growth and Differentiation Factor (e.g. GDF 5) etc. and also combinations thereof and/or other drug including a non-proteinaceous drug including small molecules (e.g. biphosphonates), possibly in combination with a proteinaceous drug, etc.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), submicron (nanofillers as from precipitation, preferentially plate like aspect ratio >10, 10-50 nm, contents 0.5 to 5% by volume).

A specific example of a material with which experiments were performed was PLDLA 70/30 comprising 30% (weight percent) biphase Ca phosphate that showed particularly advantageous liquefaction behaviour.

The material of the implant (which may be a bone screw) may be any material that does not melt at the melting temperatures of the liquefiable material. Especially, the implant may be of a metal, for example a titanium alloy. A preferred material is titanium grade 5. This material, in addition to being generally suited for implantable devices, has a comparably low heat conduction. Because of this low heat conduction, the melting zone arising in liquefiable material and at the interface to the directing structure is heated quickly, without the surroundings being heated to too high temperatures. Alternative materials for the sheath element are other metals like other titanium alloys, stainless steel, ceramics like Zirconium oxides or Aluminium oxides, or hard plastics such as PEEK etc.

An augmentation pin may or may not include a closing plug, wherein the closing plug may be fixedly attached to a leading end of a pin made of augmentation material or may be provided as a separate element so that a combination of a closing plug with a pin made of augmentation material may be formed within an augmentation implant by inserting firstly the closing plug and secondly the pin.

An augmentation pin may be inserted through the sleeve so that the augmentation pin is aligned with the axial through-bore of the sleeve and an axial through bore of the implant, and may be pushed for example by a sonotrode of an ultrasound applicator through the axial through bore in a direction to the intended implant portion at which the material of the augmentation pin shall be fluidized. A trailing end of an implant may be coupled to the sleeve.

For example, the augmentation implant may be an augmentation screw, wherein the augmentation material may be pressed from the inside of the screw to the outside so as to surround at least partially, for example, the outer thread of the screw. According to another example, the augmentation implant may be any kind of nail or bolt the outer surface of which is not provided with a thread, but which may be provided with ribs or protrusions, thus may be also non-circular. It is noted, that the augmentation implant may also be a plate for stabilizing for example a fractured object at an outer surface thereof, wherein additional material may be provided so as to extend from the plate into at least one cavity formed in the object beneath the plate.

According to an embodiment, the lateral opening of the augmentation sleeve may be formed as a slot commencing from a leading end surface of the augmentation sleeve and extending in an axial direction of the augmentation sleeve. Depending on the intended application, the lateral opening of the augmentation sleeve may be a single lateral opening with a specific width or may be a combination of two lateral openings which are formed in direct vicinity to each other.

According to an embodiment, the augmentation sleeve may further comprise an interface for connecting the augmentation sleeve to an augmentation implant. In other words, the body portion of the sleeve may be designed so that the augmentation implant, for example a bone screw, can be handled by means of the sleeve, i.e. can be held and accurately positioned at an installation site at an object and/or can be driven in into the object. In other words, the body portion of the sleeve may serve as a grip of a screwdriver or as a grip for holding an augmentation nail while punching the nail into an object. Consequently, the sleeve may comprise an interface being formed to transmit rotational forces from the augmentation sleeve to a bone screw. It is noted that these forces may also be translational forces as well as a combination of rotational and translational forces, depending on the kind of the implant.

For augmenting the implant, an ultrasound applicator may be provided having an ultrasound transducer and a sonotrode, wherein the ultrasound applicator may be arranged so that the sonotrode extends from the ultrasound transducer in a direction toward the implant portion. The ultrasound applicator may be capable of fluidizing the material of the augmentation pin within the augmentation implant by means of a combination of pressure and ultrasound vibrations, and pressing the fluidized material through at least one bore out of the implant. It will be understood that at least the sonotrode of the ultrasound applicator is movably arranged to be capable of pushing an augmentation pin through the sleeve and of pressing the material of the augmentation pin out of the implant when the material of the augmentation pin is fluidized.

According to an embodiment, the augmentation sleeve may further comprise a mark indicating the position of the lateral opening on the circumference of the sleeve. Such a mark may facilitate a positioning of the sleeve at the trailing end of the augmentation implant in an orientation such that an augmentation can be provided in a specific direction.

The augmentation sleeve may further comprise a stop for controlling the axial position of the augmentation tool in the augmentation sleeve. The stop may be a shoulder formed by different diameters in the through bore of the sleeve, at which shoulder a corresponding protrusion of the augmentation tool may abut to control the axial position.

According to another embodiment, the axial bore of the augmentation implant, for example the bone screw, may be formed as an axial through bore, wherein the bone screw further comprises an insert providing a counter surface for an augmentation of the trailing end portion of the bone screw. Such an insert may be provided as a closing plug connected to a pin of augmentation material so that the insert may be easily inserted into the augmentation implant together with the augmentation material.

According to an embodiment, the augmentation implant may be a bone screw and in particular a headless bone screw which may be completely inserted into a bone.

It is noted that an implant may be augmented by means of a plurality of augmentation pins, wherein these pins may be provided in a pin magazine. Each of the augmentation pins may be pushed into the implant by means of the sonotrode of the ultrasound applicator.

A description in more detail of steps performed while operating the sleeve together with the augmentation implant follows in conjunction with the detailed description of an exemplary embodiment below.

It has to be noted that embodiments of the invention are described with reference to different subject-matters. In particular, some embodiments are described with reference to a method, whereas other embodiments are described with reference to a device, however, a person skilled in the art will gather from the above and the following description that, unless otherwise notified, in addition to any combination of features belonging to one type of subject-matter, also any combination of features relating to different subject-matters is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION OF EXEMPLARY EMBODIMENTS

Figure 1:
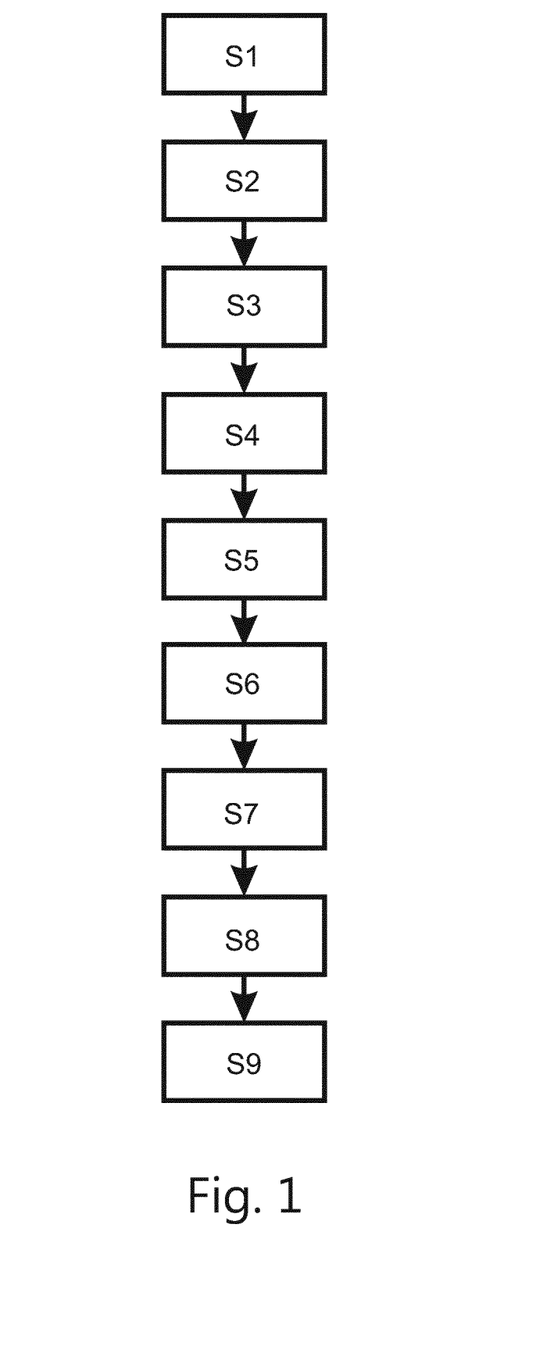
FIG. 1 is a flow chart illustrating steps of a method of operating a sleeve together with a bone implant.

The flow chart in FIG. 1 illustrates the principles of using the augmentation sleeve in accordance with the invention, i.e. illustrates the principles of augmenting a bone screw as an example of an augmentation implant. It will be understood that the steps described with respect to the method, and also with respect to FIGS. 2 to 6, are major steps, wherein these major steps might be differentiated or divided into several sub-steps. Furthermore, there might be also sub-steps between these major steps. Therefore, a sub-step is only mentioned if that step may be important for the understanding of the principles of the method.

In step S1, an implant like a bone screw is inserted into a bone. In particular, the implant may be inserted into a bone in a direction being inclined, i.e. neither perpendicular nor parallel to the outer surface of the bone. Furthermore, the implant may be inserted into a bone such that the implant extends through soft bone tissue like cancellous bone and the leading end of the implant is in contact and/or engages hard tissue like cortical bone.

In step S2, the leading end portion of the augmentation sleeve is connected with the trailing end portion of the implant, for example as a slight press fit or by means of a snap locking mechanism. It will be understood that the sleeve may also be connected to the implant before inserting the implant into bone, when using the sleeve as inserting tool.

In step S3, a closing plug is inserted into the implant to provide a counter surface for the first augmentation step. This step will in particular be performed in a case in which the implant includes an axial through bore, for example so as to be inserted over a guide wire like a Kirschner wire. It will be understood that the implant may provide a shoulder for abutment of the closing plug inside the implant at a desired position.

In step S4, augmentation material is inserted through the sleeve into the implant and the implant is augmented by pressing melted augmentation material out of lateral bores of the implant. The augmentation may be provided for example by connecting an ultrasound applicator to the sleeve such that a sonotrode of the ultrasound applicator is in contact with the augmentation material in the implant and/or the sleeve. The ultrasound applicator may be configured to melt the augmentation material by applying ultrasonic vibrations together with a predetermined force to the augmentation material so that the material is fluidized and can be pressed out of the lateral bores of the augmentation implant.

In step S5, the augmentation material which has been pressed out of the plurality of lateral bores of the implant is hardened. For example, the augmentation material will harden as soon as the material cools down within the tissue surrounding the implant and also within the implant, when stopping the application of energy by means of the ultrasound applicator.

In case of an inclined orientation of the implant, it may be desirable to further augment the side portion of the implant which is located with a distance to hard bone tissue. In such a case, the sleeve is adjusted in step S6 so that the lateral opening at the leading end of the sleeve is directed to that side portion.

It will be understood that the ultrasound applicator may be pulled back to enable an insertion of a further augmentation pin aligned with the axial through bore in the sleeve, and may afterwards again be connected to the sleeve.

In step S7, the implant is further augmented by pressing melted augmentation material out of the lateral opening of the sleeve. The hardened material inside the implant which has been introduced during the first augmentation step may form a counter surface for softening the material during a second augmentation step.

In step S8, the sleeve is removed from the implant.

In step S9 which may be an optional step, excessive augmentation material which protrudes over the outer surface of the bone is removed.

FIGS. 2 to 6 illustrate an exemplary sequence of operating a sleeve as an aid to augment an augmentation bone screw.

Figure 2:
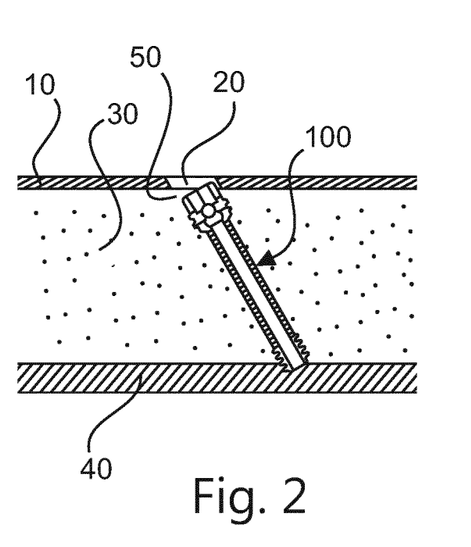
FIG. 2 is a schematically illustration of a bone implant in a bone.

In a first instance, shown in FIG. 2, a bone screw 100 is inserted into a bone including a first region 10 of hard bone tissue, i.e. cortical tissue, a second region 30 of soft bone tissue, i.e. cancellous tissue, and a third region 40 of hard bone tissue, i.e. cortical tissue. In the hard bone tissue of the first region 10, an opening 20 is formed, wherein the opening 20 may be drilled before inserting the bone screw. Through the opening 20, the bone screw 100 is inserted into the bone such that the outer thread at the leading end of the bone screw engages the third region 40.

In case the screw is inserted using a guide wire, the guide wire is removed after inserting the screw.

Figure 3:
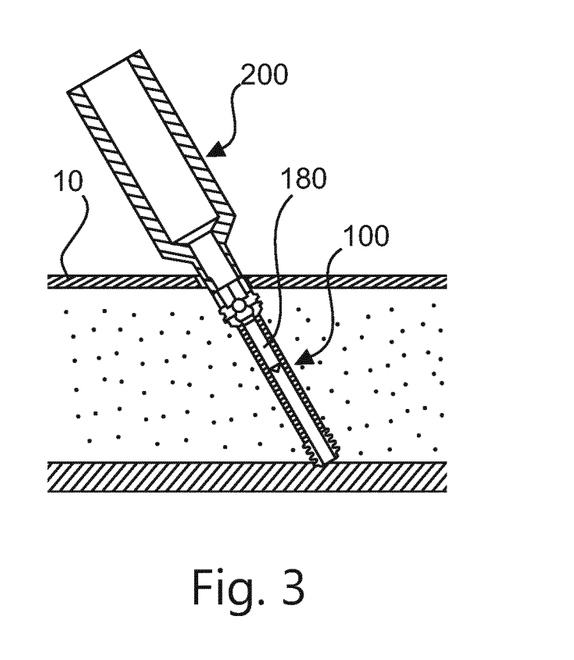
FIG. 3 is an illustration of a sleeve attached to a bone implant in a bone.

In a second instance, shown in FIG. 3, a sleeve 200 is connected to the trailing end of the screw 100, with the axis of the sleeve being substantially parallel to the axis of the screw to facilitate an access of the channel or through bore in the screw. Furthermore, a closing plug 180 is inserted into the screw such that the channel or through bore is closed.

Figure 4:
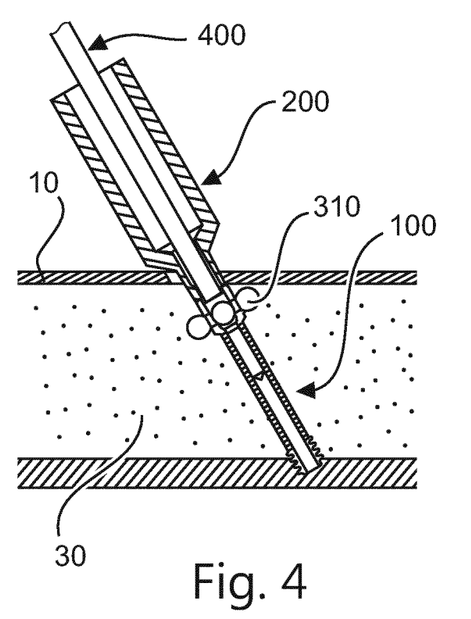
FIG. 4 is an illustration of a combination of a sleeve and a bone implant after a first augmentation step.

In a third instance, shown in FIG. 4, augmentation material is inserted into the sleeve and the trailing end of the screw above the closing plug, and is fluidized and is pressed through lateral bores out of the screw to formed first enlargements 310, by means of an augmentation tool 400. It will be understood that the enlargements 310 formed by the augmentation material are depicted as bubbles for mere illustrative purposes and that the fluidized augmentation material will fill any cavities formed in the more or less porous tissue of the region 30 of soft bone tissue.

As can be seen in FIG. 4, the inclination of the screw within the bone results in a distribution of augmentation material in which material is arranged beneath and in contact with the hard bone tissue of the first region 10 on the right side of the trailing end of the screw in FIG. 4, whereas the augmentation material which is flown out at the opposite side of the trailing end of the screw is not in contact with the hard bone tissue.

Consequently, a void 50 results between the hard bone tissue, i.e. the cortex, and the augmentation material in the bone if the screw is inserted obliquely into the bone.

Figure 5:
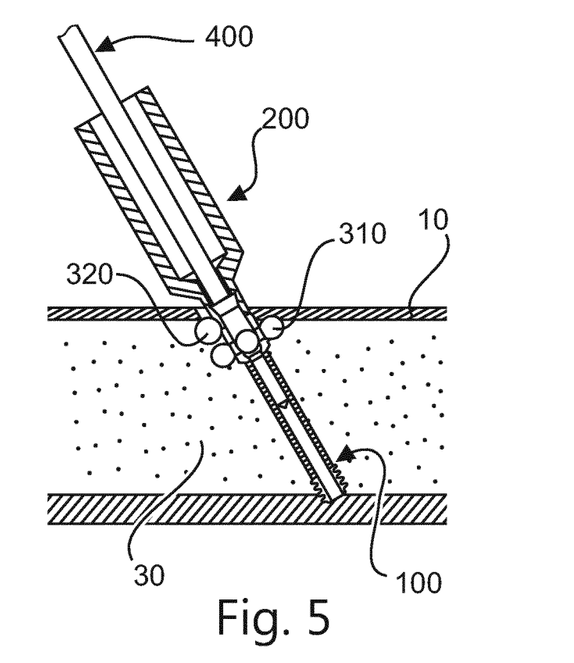
FIG. 5 is an illustration of a combination of a sleeve and a bone implant after a second augmentation step.

In a fourth instance, shown in FIG. 5, a further augmentation step has been performed causing a second enlargement 320 filling the void 50. The combination of the first enlargements 310 and the second enlargement 320 provide an improved structural support for the screw beneath the first bone region 10 of hard bone tissue, thus avoiding cut-out effects or fragment collapse of the treated bone.

Figure 6:
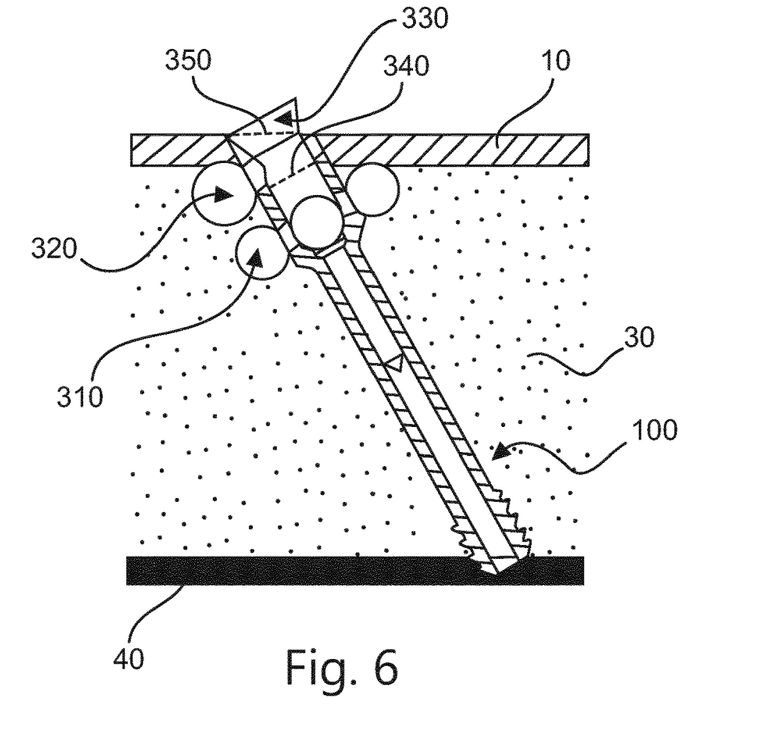
FIG. 6 is an enlarged view of an augmented bone implant.

In a fifth instance, shown in FIG. 6, the sleeve is removed, wherein augmentation material fills the trailing end of the screw and is forming the first enlargement 310 and the second enlargement 320. In case the screw is augmented in two steps, the material inserted by the first augmentation step may fill the screw up to the dotted line 340 and the material inserted by the second augmentation step protrudes out of the trailing end of the screw. The augmentation material may even protrude out of the bone, as indicated by the reference number 330. If desired, the material protruding out of the bone may be removed along the dotted line 350 to provide a smooth surface together with the outer bone surface, thus reducing any irritations of tissue surrounding the bone.

Figure 7A:
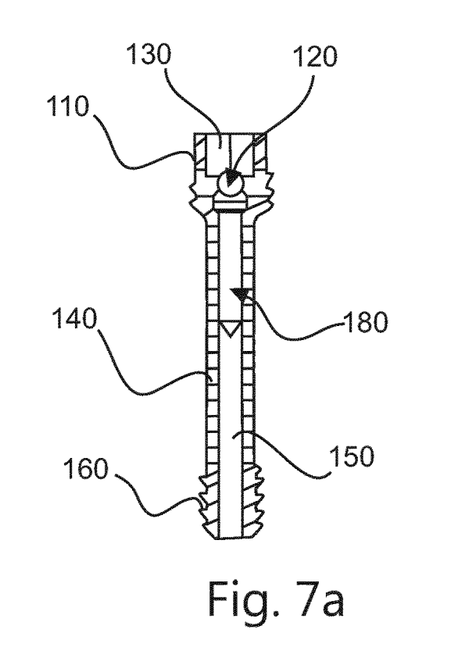
FIG. 7a is a side view in section and FIG. 7b is an isometric view of an augmentation bone screw.
Figure 7B:
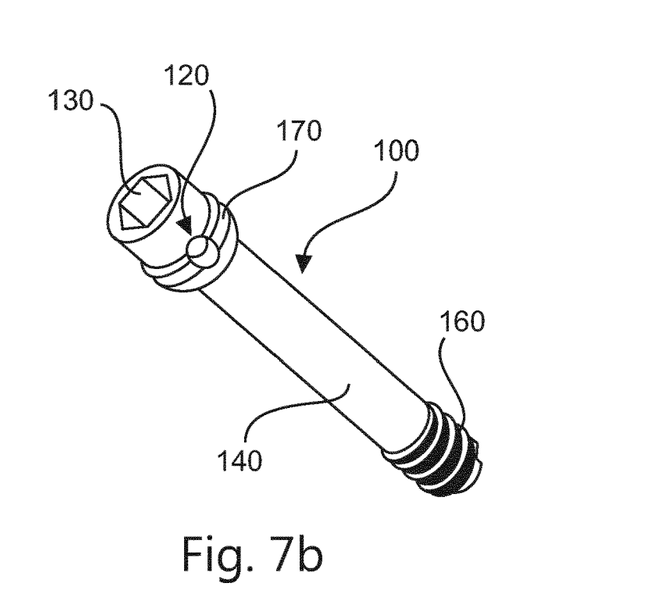

FIGS. 7a and 7b show an embodiment of a bone screw configured to be augmented at its trailing end. The bone screw 100 comprises a head portion 110 with lateral bores 120 and an inner tool engagement portion 130 such as hexagonal socket, and a shaft 140 with an axial through bore 150 and an outer thread 160 at the leading end portion of the shaft. The head portion 110 at the trailing end of the screw may have an outer diameter which is only slightly larger than the outer diameter of the shaft 140 so that the screw may be denoted as headless screw and can be completely inserted into a bone.

Furthermore, an additional outer thread 170 may be provided at the head portion, allowing further engagement of the bone screw in bone tissue also at the trailing end of the screw. As shown in FIG. 7a, a closing plug 180 may be inserted into the axial through bore 150 of the shaft so that the through bore 150 is closed adjacent the lateral bores 120, thus allowing an augmentation of the trailing end portion including the head portion 110 of the screw 100.

Figure 8A:
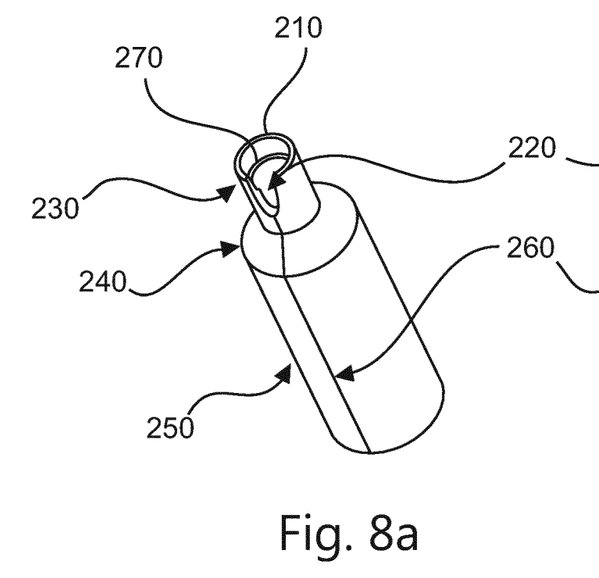
FIG. 8a is an isometric illustration and FIG. 8b a side view of a slotted sleeve according to a first embodiment.
Figure 8B:
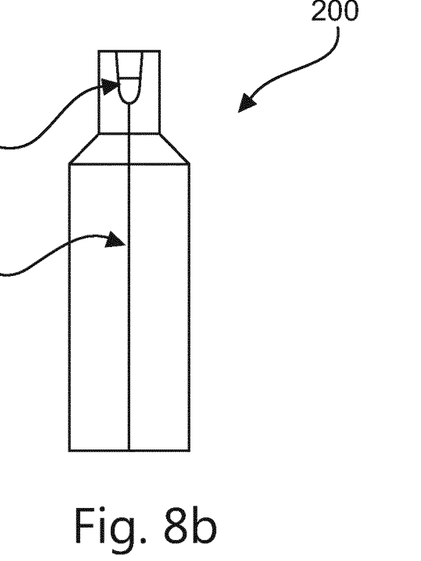

FIGS. 8a and 8b show a first embodiment of a hollow augmentation sleeve. The sleeve 200 comprises a cylindrical body 250 with a first diameter and a tip portion 230 with a second diameter, wherein the first diameter is larger than the second diameter. Between the cylindrical body 250 and the tip portion 230, a conical portion 240 may be provided as a transition. The tip portion 230 is formed with a small wall thickness and has a front surface 210, wherein a slot 220 commences from that front surface 210 and extends in a direction to the cylindrical body 250. In other words, the slot or lateral opening 220 in the tip portion 230 of the sleeve 200 is open not only laterally but also in a direction to the front end or front surface 210 of the sleeve. Because of the open slot, the sleeve is removable after an augmentation and particularly after hardening of the augmentation material. The slot 220 may be slightly widened on moving toward the open end for easier removal and better outflow behaviour.

The embodiment of FIGS. 8a and 8b may be mounted on an outside of a head portion at a trailing end of a bone implant. In the tip portion 230 of the sleeve, a shoulder 270 formed as an inner step facing the leading end of the sleeve may be provided, the step being formed between two different inner diameters. The shoulder may abut onto an end face of the head portion of the implant. The shoulder 270 may be arranged approximately in the middle of the slot, measured in a longitudinal direction of the sleeve, so that a lateral opening will remain even if the sleeve is mounted onto an implant.

Figure 9A:
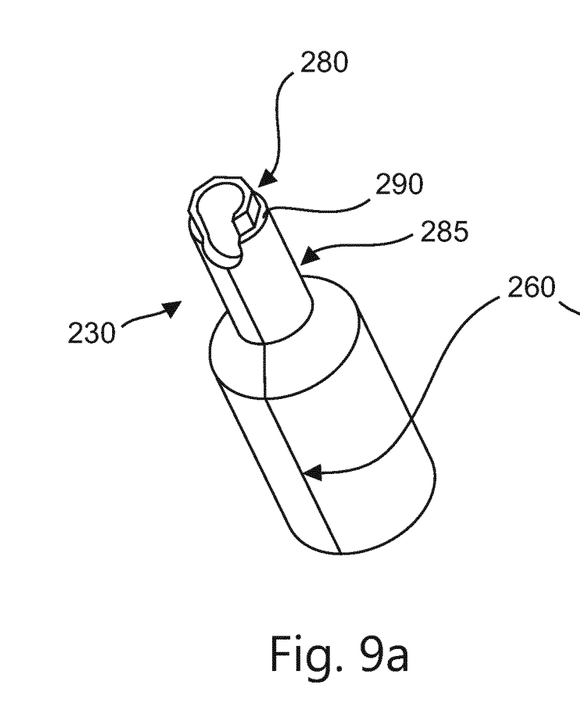
FIG. 9a is an isometric illustration and FIG. 9b a side view of a slotted sleeve according to a second embodiment.
Figure 9B:
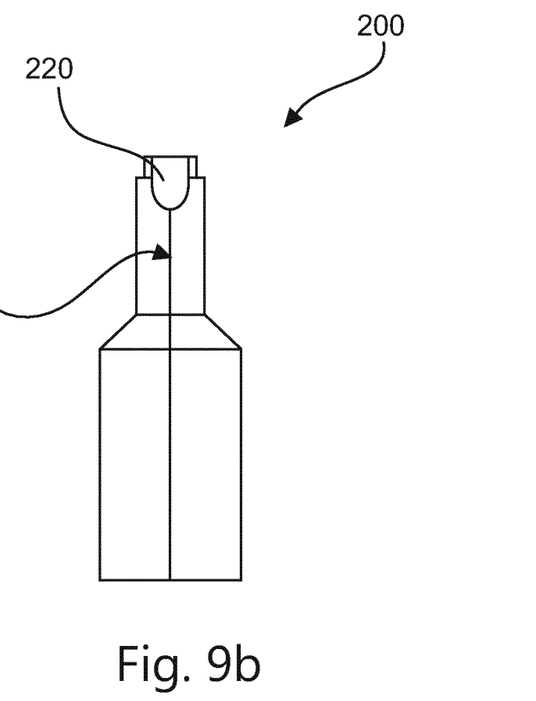

FIGS. 9a and 9b show a second embodiment of a hollow augmentation sleeve. The sleeve according to the second embodiment is comparable to the sleeve according to the first embodiment, except for the tip portion 230 which is formed with an outer tool engagement portion 280 like a hexagonal interface. The outer tool engagement portion 280 may be configured to be inserted into an inner tool engagement portion 130 at the trailing end of an implant, particularly of a bone screw so as to transmit rotational forces from the sleeve to the screw. The outer tool engagement portion 280 is limited by an outer shoulder 290 which is formed between a cylindrical portion 285 of the tip portion 230 and the tool engagement portion 280 having a reduced diameter relative to the cylindrical portion 285. Also here, the shoulder is arranged approximately in the middle of the slot 220 so that a lateral opening is provided when the sleeve is mounted at a trailing end or a bone screw.

The first embodiment as well as the second embodiment of an augmentation sleeve 200 comprises a mark 260 indicating the position of the slot 220 on the circumference of the sleeve. By the mark 260, a lateral orientation of the slot may be identified even if the slot is not visible, for example when the sleeve is mounted at an end of an implant and is protruding into tissue surrounding a bone. The mark facilitates the positioning of the sleeve with the lateral slot being in a specific orientation as it might be desired in a case as depicted in FIGS. 2 to 6.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

LIST OF REFERENCE SIGNS 10 first bone region
20 opening
30 second bone region
40 third bone region
50 void
100 bone screw
110 head portion
120 lateral bore
130 inner tool engagement portion
140 shaft
150 axial through bore
160 outer thread
170 outer thread
180 closing plug
200 sleeve
210 front surface
220 lateral slot
230 tip portion
240 transition portion
250 cylindrical body 260 mark
270 inner shoulder
280 outer tool engagement portion
285 cylindrical portion
290 outer shoulder
310 first enlargement
320 second enlargement
330 protruding augmentation material
340 transition between first and second augmentation
350 smooth surface
400 augmentation tool

The invention claimed is:

1. A surgical system comprising a combination of a bone implant and an augmentation sleeve;
the bone implant comprising a leading end portion, a trailing end portion, an axial bore and a plurality of lateral bores formed on a circumference of the bone implant;
the augmentation sleeve comprising a tip portion which is adapted to be coupled to the trailing end portion of the bone implant, and a lateral opening at the tip portion;
wherein the augmentation sleeve is adapted to guide an augmentation tool to the trailing end portion of the bone implant and to the tip portion of the augmentation sleeve so as to augment the trailing end portion of the bone implant through the plurality of lateral bores of the bone implant by a first enlargement and through the lateral opening of the augmentation sleeve by a second enlargement, wherein the first enlargement is arranged at least partially at a different axial position than the second enlargement; and
wherein the augmentation sleeve is further adapted to be removed after the augmentation of the trailing end portion of the bone implant,
wherein the lateral opening of the augmentation sleeve is formed as a slot commencing from a leading end surface of the augmentation sleeve and extending in an axial direction of the augmentation sleeve.

2. The combination of claim 1, wherein the augmentation sleeve further comprises an interface for connecting the augmentation sleeve to the bone implant.

3. The combination of claim 2, wherein the interface is formed to transmit rotational forces from the augmentation sleeve to the bone implant.

4. The combination of claim 1, wherein the augmentation sleeve further comprises a mark indicating the lateral position of the lateral opening.

5. The combination of claim 1, wherein the augmentation sleeve further comprises a stop for controlling the axial position of the lateral opening relative to the bone implant.

6. The combination of claim 1, wherein the bone implant further comprises a closing plug providing a counter surface for the augmentation of the trailing end portion of the bone implant.

7. The combination of claim 1, wherein the bone implant is a bone screw, in particular a headless bone screw.

8. A method of operating the combination of a bone implant and an augmentation sleeve according to claim 1, the method comprising the steps of:
inserting the bone implant into a bone;
connecting the tip portion of the augmentation sleeve with the trailing end portion of the bone implant;
augmenting the trailing end portion of the bone implant by pressing melted augmentation material out of the plurality of lateral bores of the bone implant, adjusting the augmentation sleeve to direct the lateral opening to a specific direction, further augmenting the trailing end portion of the bone implant by pressing melted augmentation material out of the lateral opening of the augmentation sleeve; and
removing the augmentation sleeve.

9. The method of claim 8, wherein the augmentation material which has been pressed out of the plurality of lateral bores is hardened before the trailing end portion of the bone implant is further augmented.

10. The method of claim 8, further comprising the step of inserting a closing plug into the bone implant to provide a counter surface for the step of augmenting the trailing end portion of the bone implant by pressing melted augmentation material out of the plurality of lateral bores of the bone implant.

11. The method of claim 8, further comprising the step of removing excessive augmentation material.

12. The system of claim 1 further comprising a polymer rod slidably received in the through bore of the augmentation sleeve.

13. The system of claim 12 further comprising a sonotrode mountable on the augmentation sleeve for providing ultrasonic energy to the polymer pin.

14. The combination of claim 1 wherein the axial bore in the bone implant is a through bore.

15. A surgical system comprising:
a bone screw and an augmentation sleeve;
wherein the bone screw comprises a leading end portion and an enlarged trailing end portion, the trailing end having an axially extending hollow interior portion, the hollow interior portion having first and second axially spaced bores extending laterally from the hollow interior of the enlarged trailing end to an outer surface of the enlarged trailing end, the first laterally extending bore closer to the trailing end of the bone screw than the second laterally extending bore, an axial through bore extending from the leading end portion of the bone screw to the hollow interior portion; and
wherein the augmentation sleeve comprises a tip at a leading end thereof configured to be received in the hollow interior portion of the bone screw, the augmentation sleeve having a through bore extending from a leading end to a trailing end thereof, the augmentation sleeve leading end having an opening extending from the through bore to an outer surface of the augmentation sleeve, the opening in the leading end of the augmentation sleeve capable of being aligned with the first laterally extending bore of the bone screw and the tip of the augmentation sleeve being spaced axially from the second laterally extending bore of the bone screw toward the trailing end of the bone screw when the tip is received in the hollow interior portion of the trailing end of the bone screw
wherein the tip at the leading end of the augmentation sleeve has an interface configured to transmit rotational forces from the augmentation sleeve to the bone screw.

16. The system of claim 15, wherein the augmentation sleeve further comprises a stop surface for controlling the axial position of the opening at the leading end of the augmentation sleeve relative to the bone screw.

17. The system of claim 15, wherein the bone screw further comprises a closing plug providing a counter surface for the augmentation of the trailing end portion of the bone screw.

* * * * *